United States Patent [19]

Angulo et al.

[11] Patent Number: 4,823,793
[45] Date of Patent: Apr. 25, 1989

[54] CUTTING HEAD FOR ULTRASONIC LITHOTRIPSY

[75] Inventors: Earl D. Angulo, Silver Spring, Md.; Roger Goodfriend, Los Gator, Calif.

[73] Assignee: The United States of America as represented by the Administrator of the National Aeronuautics & Space Administration, Washington, D.C.

[21] Appl. No.: 793,006
[22] Filed: Oct. 30, 1985
[51] Int. Cl.⁴ ............................................. A61B 17/22
[52] U.S. Cl. .................................... 128/328; 128/24 A
[58] Field of Search .............................. 128/24 A, 328

[56] References Cited

U.S. PATENT DOCUMENTS

| | | | |
|---|---|---|---|
| 3,823,717 | 7/1974 | Pohlman et al. | 128/138 |
| 3,830,240 | 8/1974 | Antonevich et al. | 128/138 |
| 3,857,396 | 12/1974 | Hardwick | 128/335 |
| 3,896,811 | 7/1975 | Storz | 128/138 |
| 4,178,935 | 12/1979 | Gekhman et al. | 128/138 |
| 4,474,180 | 10/1984 | Angulo | 128/24 A X |
| 4,572,184 | 2/1986 | Stohl et al. | 128/328 |

*Primary Examiner*—Michael H. Thaler
*Attorney, Agent, or Firm*—R. D. Marchant; John R. Manning; John O. Tresansky

[57] ABSTRACT

A cutting head for attachment to the end of the wire probe of an ultrasonic kidney stone disintegration instrument. The cutting head has a plurality of circumferentially arranged teeth formed at one end thereof to provide a cup-shaped receptacle for kidney stones encountered during the disintegration procedure. An integral reduced diameter collar diminishes stress points in the wire and reduces breakage thereof.

7 Claims, 1 Drawing Sheet

CUTTING HEAD FOR ULTRASONIC LITHOTRIPSY

ORIGIN OF THE INVENTION

The invention described herein was made by an employee of the U.S. Government and another and may be manufactured and used by or for governmental purposes without the payment thereon or therefor.

TECHNICAL FIELD

This invention relates to surgical apparatus for disintegrating urinary calculi, and, more particularly, to a cutting head and to an ultrasonic device for fragmenting or drilling through urinary calculi in situ.

BACKGROUND ART

The incidence of hospitalization for the removal of urinary calculi, commonly referred to as kidney stones, has been estimated to be as high as 200,000 cases per year. Stones which are quite small may in some cases be passed without hospitalization. However, in the remainder, the kidney stones become impacted in the ureter, a muscle tube joining the kidney to the bladder. An impacted kidney stone is a source of intense pain and bleeding, a source of infection, and, if the stone completely blocks the flow of urine for any extended length of time, can cause the loss of a kidney. Small stones which are lodged in the lower third of the ureter can be removed non-surgically by using a technique employing the well known Dormia stone basket. However, basket removal of a kidney stone usually fails if the stone is lodged in the upper ureter, is impacted, or is larger than one centimeter in diameter. In these cases, the only procedure by which the stone could heretofore be removed was through a serious surgical operation called a ureterolithotomy.

More recently, however, a non-surgical method for removing kidney stones has been developed. In this technique, the kidney stones are subject to a vibratory action, such as that provided by an ultrasonically vibrated wire probe. In one such apparatus, a catheter is placed cystoscopically at the site of the stone in the urinary tract, after which a long wire probe is passed through a lumen of the catheter and is brought into contact with the stone. The wire probe is attached to the ultrasonic transducer which, when energized, sets the wire probe into lateral and longitudinal vibrations. The vibrational energy is transmitted by the wire probe to the stone, causing it to fracture into small fragments which the patient can then pass spontaneously after withdrawal of the catheter.

While such apparatus can perform its intended function, a severe limitation has been found to exist due to slippage of the thin wire probe off the kidney stone and its lodgement between the stone and urinary tract. Attempts to ameliorate this situation by providing a wider tip cutting surface has resulted in premature breakage of the wire probe at the tip exiting the catheter near the kidney stone. This occurs because the vibrational energy, typically 20 KHz in frequency, in conjunction with the added cantilevered mass of the larger cutting area, causes the wire probe to snap off due to metal fatigue after 10-20 seconds of operation. This has been found to be insufficient time to complete the disintegration procedure, as well as dangerous because it leaves metal fragments in the urinary tract. A clear need, therefore, exists to prolong the operational life of the wire probe for a length of time adequate for completion of the procedure. A desirable time frame is typically one minute, which is substantially greater than that provided by known prior art apparatus.

STATEMENT OF THE INVENTION

Accordingly, it is an object of the invention to provide a cutting head for surgical use.

Another object of the present invention is to provide a cutting head member for an ultrasonically vibrated wire probe.

A further object of the instant invention is to provide a safer and more efficient cutting head for ultrasonically disintegrating kidney stones.

Still another object of the invention is to provide an improved system for prolonging the operational life of an instrument for disintegrating kidney stones.

Another further object of the present invention is to provide a device for seating of kidney stones within a cutting head in an ultrasonic lithotripsy procedure.

Yet another object of the present invention is to greatly enhance the fragmentation of kidney stones when using ultrasonic lithotripsy.

These and other objects of the present invention are provided by a cutting head which is attachable to the end of the ultrasonically vibrated wire probe. The cutting head includes a large diameter cutting section provided with a plurality of teeth formed on the periphency of one end thereof to present a cup-shaped receptacle to seat a kidney stone thereon. The member also includes a collar integrally formed with the cutting tip section to reduce stress points along the probe.

BRIEF DESCRIPTION OF THE DRAWINGS

The foregoing, as well as other objects, features, and advantages of the invention will become apparent from the following detailed description when taken in conjunction with the appended drawings in which like numbers represent the same or similar components throughout the several drawings, and wherein.

DESCRIPTION OF THE PREFERRED EMBODIMENT

Figure 1:
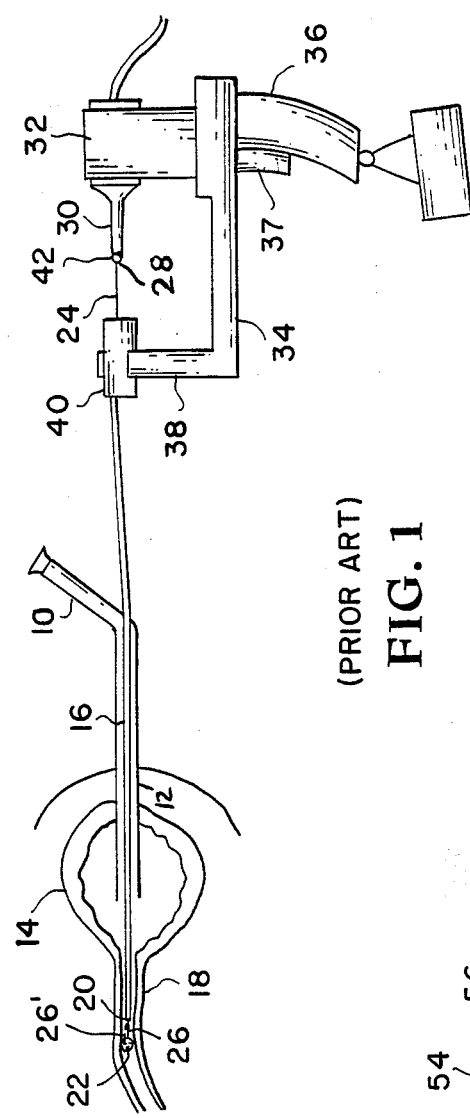
FIG. 1 is a side elevational view of state-of-the-art apparatus for fragmenting kidney stones.

Referring to the drawings, and, more particularly, to FIG. 1, there is illustrated an ultrasonic kidney stone disintegration instrument in accordance with the prior art. The purpose of this Figure is to provide a better understanding of the invention to be described in detail in conjunction with FIGS. 2 and 3.

FIG. 1 shows a cystoscope 10 inserted through a patient's urethra 12 into a bladder 14. A catheter 16 is inserted through the cystoscope 10, the bladder 14, and into a ureter 18 until its far end 20 comes into proximity to a piece of urinary calculi, hereinafter referred to as a kidney stone, 22. A wire probe 24 is inserted through the catheter 16 until its far end 26 contacts the stone 22. The diameter of the wire probe 24 is substantially smaller than the lumen diameter of the catheter 16 so that any movement of the wire probe is not restricted by the catheter material. The opposite, or near end, 28 of the wire probe 24 is connected to the tip 30 of a movable ultrasonic transducer assembly 32 which is mounted on a base 34. The base 34 includes a handle 36 having a trigger 37 which is connected to the transducer 32 for adjusting the position of the wire probe 24 against the stone 22 by a linear translation of the transducer assembly 32 on the base 34. Base 34 additionally includes an outward angular support member 38 which includes a connector element in the form of a catheter joint 40 for engaging and holding the near end of the catheter 16. The terminal portion of the wire probe is clamped to tip 30 of the transducer 32 by a set screw 42.

With the catheter 16 and wire probe 24 inserted into the ureter 18, end 26 of the probe is optically guided to make contact against kidney stone 22. Thereafter, the transducer assembly 32 is energized to provide lateral motion to the wire probe 24 and the probe is gently pushed against the stone.

This apparatus does not operate as desired when tip 26 of the wire probe slips off the surface of the stone 22 and slides past it as illustrated in the dotted line position of tip 26'. In this circumstance tip 26' does not perform its intended function. Increasing the surface area of the cutting tip causes it to break off from the probe 24 at end 20 of catheter 16, at the point of greater stress where it emerges from the catheter.

Figure 3:
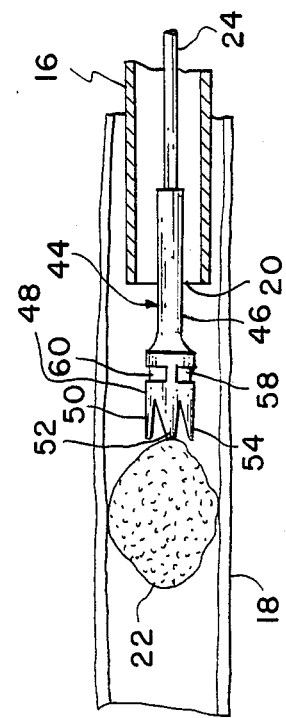
FIG. 3 is a longitudinal view, partly in section, of the cutting head in contact with a kidney stone.
Figure 2:
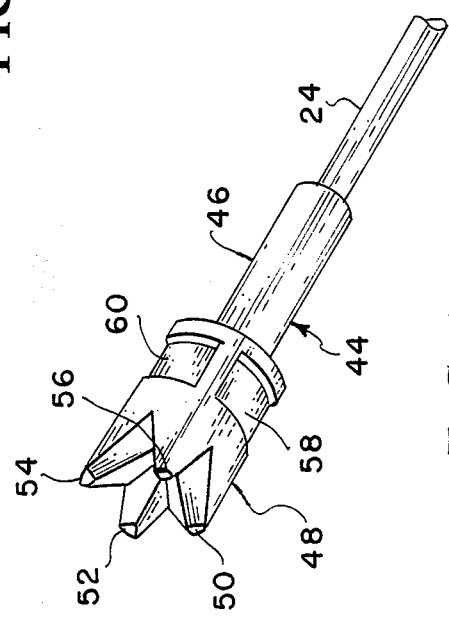
FIG. 2 is a side elevational view of the cutting head of this invention.

With the foregoing in mind, a cutting tip 44 shown in FIGS. 2 and 3 is attached to end 26 of the wire probe to overcome the problem of wire slippage and to greatly increase the cutting surface area. Tip member 44 provides two structural features, one of which prevents premature breakage of the wire probe at the point of its exiting the catheter 16, while the other assures seating of the kidney stone within the tip member 44.

Member 44 is of stainless steel construction and comprises two integrally formed coaxial cylindrical sections, an elongate collar section 46 which relieves stress, and a cutting tip section 48.

Member 44 is also provided with a central circular opening (not shown) which extends completely through collar section 46 and through most of cutting tip section 48. The opening has a diameter sufficiently wide so that it is just capable of being slid over wire tip 26. By inserting wire tip 26 through the opening as far as possible into the cutting tip section 48, the end of the cutting tip section is arranged to initially abut the kidney stone encountered. Member 44 is thereafter compressed and swaged to the wire probe 24, such as at points 58 and 60 of the cutting tip section 48, thereby ensuring its permanent retention thereon. Additionally, tip 26 can be undercut so as to present a recessed surface, further enhancing the swaging procedure.

Collar section 46, has an external diameter larger than that of probe 24, but less than the inner diameter of catheter 16 and is of sufficient length to insure that it only partially extends out of the catheter when it is in the operational mode, best illustrated in FIG. 3.

Cutting tip section 48 has a slightly larger external diameter than the external diameter of collar section 46 but less than the inner diameter of ureter 18. It is provided with a plurality of cutting teeth, preferably between three and six. The cutting tip section 48 is illustrated in FIG. 2 as having four teeth 50, 52, 54, and 56. Teeth 50, 52, 54, and 56 are formed on the periphery of one end of the cutting tip section to provide a cup-shaped receptacle for seating a kidney stone 22. Teeth 50, 52, 54, and 56 are machined directly into the end of cutting tip section 48 and are desirably provided with flat ends so as to preclude the possibility of a pointed tooth surface from scraping the urethra. While no specific configuration for the teeth is necessary, it has been found that a suitable arrangement is one where the teeth are equidistantly-spaced, three-sided with one corner forming the cup-shaped receptacle, and with a tapering cross section.

While not intended to be limiting, the following approximate dimensions of the cutting head 44 are presented by way of example only:
Diameter of cutting tip section 48—0.063 inches
Length of cutting tip section 48—0.16 inches
Diameter of collar section 46—0.045 inches
Length of collar section 46—0.233 inches In such a configuration, the member 44 attached to the wire probe 24 transmits maximum acoustic vibrational energy from the probe to the stone 22. The relatively large diameter of cutting tip section 48 increases the cutting surface area by a factor of three or more and insures maximum contact between wire and stone 22 as well as prevents slippage of the wire past the stone. The cup-shaped end of the tip 48 induces seating of the stone 22 on the cutting tip.

The four teeth 50, 52, 54, and 56 assure maximum fragmentation of the stone 22. Even if the stone 22 is highly irregular in shape and centering of the tip 48 upon the stone is far from perfect, the stone will fragment when contacted by any portion of the cutting tip.

The lifetime of the wire probe 24 is substantially increased by the provision of an elongate collar 46 which partially stays within the catheter 16 while the cutting tip section 48 is extended against the stone 22. The collar 46 greatly lessens the mechanical bending loads and stress points imposed on the wire probe 24 by the vibrating mass of the cutting tip 48, because the root of the mass is within the catheter 16 and not cantilevered away from it. Further, by joining the cutting tip 48 to the wire probe 24 by a swaged joint 58, 60 rather than by soldering, mechanical stresses and fatigue fractures are greatly lessened. The life of the assembly has been found to exceed four minutes when vibrating at 20 KHz, thus providing ample time to complete the kidney stone disintegration procedure.

Having thus shown and described the invention in specific detail, the same has been provided by way of explanation and not limitation and accordingly all modifications, alterations and changes coming within the spirit and scope of the invention are herein meant to be included.

We claim:

1. A surgical cutting head for attachment to an ultrasonically vibrated wire probe, comprising:
   a cylindrical cutting tip section having a plurality of cutting teeth arranged circumferentially at one end thereof, said teeth being equidistantly spaced on said one end of said cutting tip section and having flat top ends and expanding three-sided cross sections along the length of said teeth to form a cup-shaped seat having inwardly projecting intersections formed by two sides of said three-sided cross sections to form cutting edges within said cup-shaped seat; and
   a cylindrical collar coaxial and integrally formed with the other end of said cutting tip section.

2. The cutting head of claim 1 wherein said collar and cutting tip sections are provided with a central bore along their common axis, said bore extending through said collar and partially through said cutting tip section whereby said head may be slid over the wire probe and swaged thereto.

3. The cutting head of claim 2 wherein the external diameter of said cutting tip section is larger than the external diameter of said collar section.

4. Surgical apparatus for disintegrating and dislodging urinary calculi lodged in the urinary tract, comprising:
- a catheter adapted to be inserted into the ureter to come into proximity of the calculi to be dislodged;
- a wire probe fed through said catheter;
- ultrasonic transducer means coupled to said wire probe for imparting vibrations thereto; and
- a cylindrical member including a cutting tip section joined to the end of said wire probe for contacting said calculi, said cutting tip section comprising a plurality of cutting teeth equidistantly spaced about the circumference of one end of said member, said teeth having flat top ends and expanding three-sided cross sections along the length of said teeth to form a cup-shaped seat to abut said calculi, said seat having inwardly projecting intersections formed by two sides of said three-sided cross sections to form cutting edges within said cup-shaped seat.

5. The apparatus of claim 4 wherein said cylindrical member further includes an elongate collar section coupled to and coaxial with said cutting tip section and wherein said member is swaged onto said wire probe.

6. The apparatus of claim 5 wherein the diameter of said wire probe is substantially less than that of said catheter and the external diameter of said collar section is at least twice as great as that of said wire probe, but less than the diameter of said catheter.

7. The apparatus as recited in claim 6 wherein said collar section partially stays within said catheter when said ultrasonic transducer is imparting vibrations to said wire probe.

* * * * *